United States Patent
Campbell et al.

(10) Patent No.: US 9,808,268 B2
(45) Date of Patent: Nov. 7, 2017

(54) MEDICAL RETRIEVAL DEVICES AND RELATED METHODS OF USE

(71) Applicant: Boston Scientific Scimed, Inc., Maple Grove, MN (US)

(72) Inventors: Andrew J. Campbell, Reading, MA (US); Mark Andrew Hera, Holden, MA (US); Richard C. Tah, Framingham, MA (US); Steven E. Walak, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 328 days.

(21) Appl. No.: 14/550,103

(22) Filed: Nov. 21, 2014

(65) Prior Publication Data

US 2015/0148813 A1     May 28, 2015

Related U.S. Application Data

(60) Provisional application No. 61/909,504, filed on Nov. 27, 2013.

(51) Int. Cl.
*A61B 17/42* (2006.01)
*A61B 17/221* (2006.01)
*A61B 17/00* (2006.01)

(52) U.S. Cl.
CPC .. *A61B 17/221* (2013.01); *A61B 2017/00964* (2013.01); *A61B 2017/2215* (2013.01)

(58) Field of Classification Search
CPC ........ A61B 17/221; A61B 2017/00964; A61B 2017/2215
See application file for complete search history.

(56) References Cited

U.S. PATENT DOCUMENTS 5,906,622 A * 5/1999 Lippitt ................. A61B 17/221 606/113
2008/0119869 A1 * 5/2008 Teague ................. A61B 17/221 606/127

* cited by examiner

*Primary Examiner* — Richard Louis
(74) *Attorney, Agent, or Firm* — Bookoff McAndrews, PLLC

(57) ABSTRACT

A medical device may include an elongate member, and a plurality of grasping members extending from the elongate member. Each of the grasping members may include a proximal end, and a distal end. Each of the grasping members may include at least one first section formed of a first material and a second material, and a second section located at the distal end of the grasping member. The second section may be formed without the first material and being less stiff than the at least one first section.

18 Claims, 4 Drawing Sheets

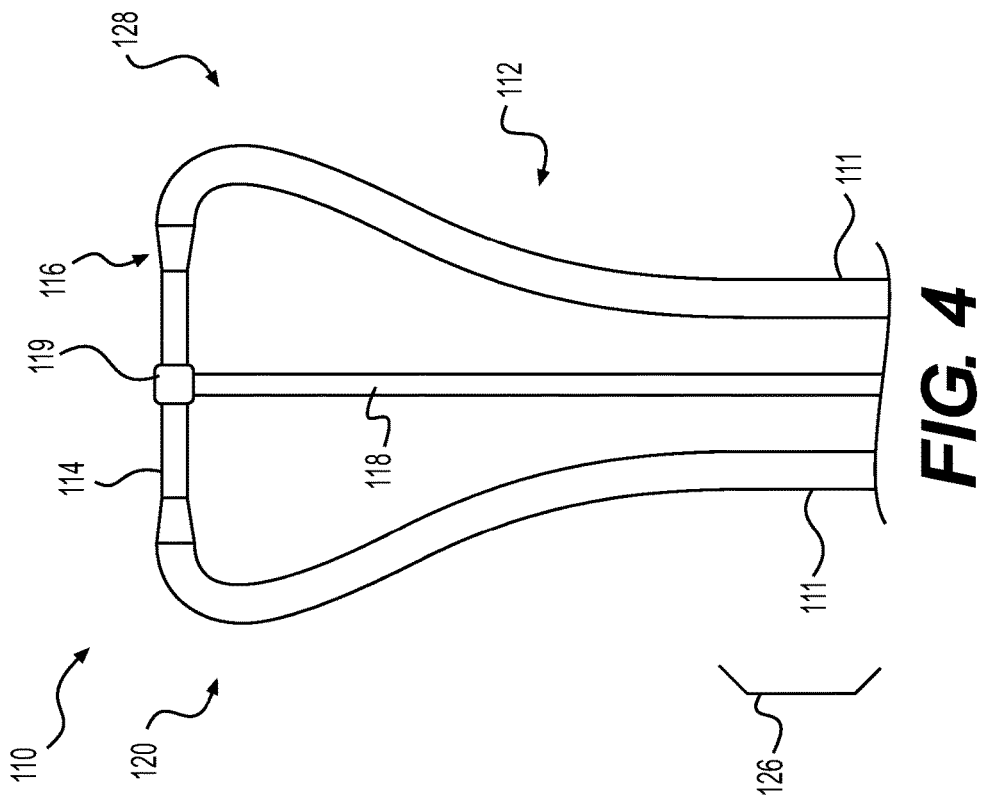
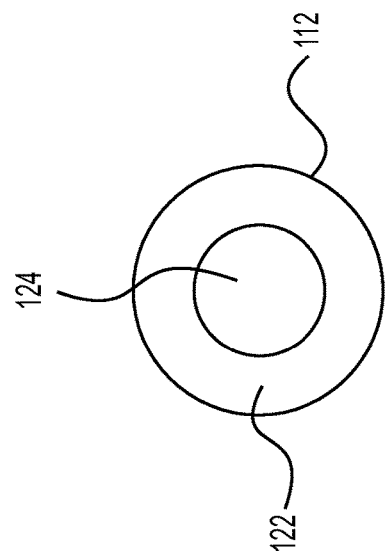
FIG. 4
FIG. 3

MEDICAL RETRIEVAL DEVICES AND RELATED METHODS OF USE

CROSS-REFERENCE TO RELATED APPLICATION

This patent application claims the benefit of priority under 35 U.S.C. §119 to U.S. Provisional Patent Application No. 61/909,504, filed Nov. 27, 2013, the entirety of which is incorporated herein by reference.

TECHNICAL FIELD

Various embodiments of the present disclosure relate generally to medical retrieval devices and related systems and methods. More specifically, the present disclosure relates to devices, systems, and methods for retrieving objects within a patient.

BACKGROUND

Medical retrieval devices are often utilized for removing organic material (e.g., blood clots, tissue, and biological concretions such as urinary, biliary, and pancreatic stones) and inorganic material (e.g., components of a medical device or other foreign matter), which may obstruct or otherwise be present within a patient's body cavities. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy (PNCL) procedure. Further, lithotripsy and ureteroscopy, for example, are used to treat urinary calculi (e.g., kidney stones) in the ureter of a patient.

Further, some medical device baskets are formed from metals contained within thin polymer tubes. During operation of the baskets, the metals slide into and out of the polymer tubes, and the repeated movements stresses and degrades the polymer tubes, resulting in decreased performance or failure.

Thus, there remains a need for improved medical retrieval devices having improved durability.

SUMMARY OF THE DISCLOSURE

The present disclosure includes medical retrieval devices and related methods of use.

In accordance with an embodiment of the disclosure, a medical device may include an elongate member, and a plurality of grasping members extending from the elongate member. Each of the grasping members may include a proximal end, and a distal end. Each of the grasping members may include at least one first section formed of a first material and a second material, and a second section located at the distal end of the grasping member. The second section may be formed without the first material and having a different stiffness than the at least one first section.

Various embodiments of the disclosure may include one or more of the following aspects: further including at least one third section disposed between the at least one first section and the second section, the at least one third section being formed of the first material and the second material, the thickness of the first material in the at least one third section being less than a thickness of the first material in the at least one first section; wherein the thickness of the first material in the at least one third section surrounds the second material in the at least one third section and tapers toward the second section; wherein the plurality of grasping members are reciprocally movable between a retracted and an expanded configuration; further including an actuation member coupled to at least one of the plurality of grasping members, wherein the movement of the actuation member moves the at least one grasping member from the retracted configuration to the expanded configuration; wherein the actuation member is coupled to the second section; wherein the plurality of grasping members bend radially outward from a longitudinal axis of the medical device in the expanded configuration; wherein the second section lies in a plane that extends substantially orthogonal to a longitudinal axis of the medical device; wherein the second section includes a bent portion; wherein, in the expanded configuration, the bent portion extends radially outward from the longitudinal axis of the medical device; wherein, in the retracted configuration, the bent portion extends radially inward toward the longitudinal axis of the medical device; further including at least one notch disposed along the at least one first section; wherein the first material is disposed around the second material in the first section; wherein the grasping member is formed from a continuous length of second material; wherein a middle region of the continuous length of second material corresponds to the second section of the grasping member; and wherein the plurality of grasping members includes three grasping members coupled to one another to form a basket or grasper.

In accordance with an embodiment of the disclosure, a medical device may include an elongate member, and a plurality of grasping members extending from the elongate member. Each of the grasping members may include a proximal end, and a distal end disposed further away from a longitudinal axis of the medical device than the proximal end. Each of the grasping members may also include at least one first section being formed of a first material having a first material property and a second material having a second material property, and a second section located at the distal end of the grasping member. The second section may be formed without the first material, and may have a different stiffness than the at least one first section.

In accordance with an embodiment of the disclosure, a medical device may include a basket or grasper having a plurality of arms movable between a refracted configuration and an expanded configuration. The basket or grasper may be formed by a plurality of grasping members. Each grasping member may include a proximal end, and a distal end. Each grasping member may also include a plurality of first sections being formed of an outer material and a core material, and a second section located at the distal end of the grasping member. The second section may be formed with only the core material, and may have a different stiffness than each of the plurality of first sections. Each of the plurality of arms may be formed by joined first sections of adjacent grasping members.

Various embodiments of the disclosure may include one or more of the following aspects: wherein a first of the plurality of arms is formed by joined first sections of a first and a second of the plurality of grasping members, a second of the plurality of arms is formed by joined first sections of the second and a third of the plurality of grasping members, and a third of the plurality of arms is formed by joined first sections of the third and the first of the plurality of grasping members; and wherein each of the plurality of arms extends radially outward about a longitudinal axis of the medical device when the basket is in the expanded configuration.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

FIG. 3 cross-sectional view of the grasping member of FIG. 2 taken along line 3-3.

FIG. 4 is a partial side view of the grasping member of FIG. 2.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts.

Figure 1:
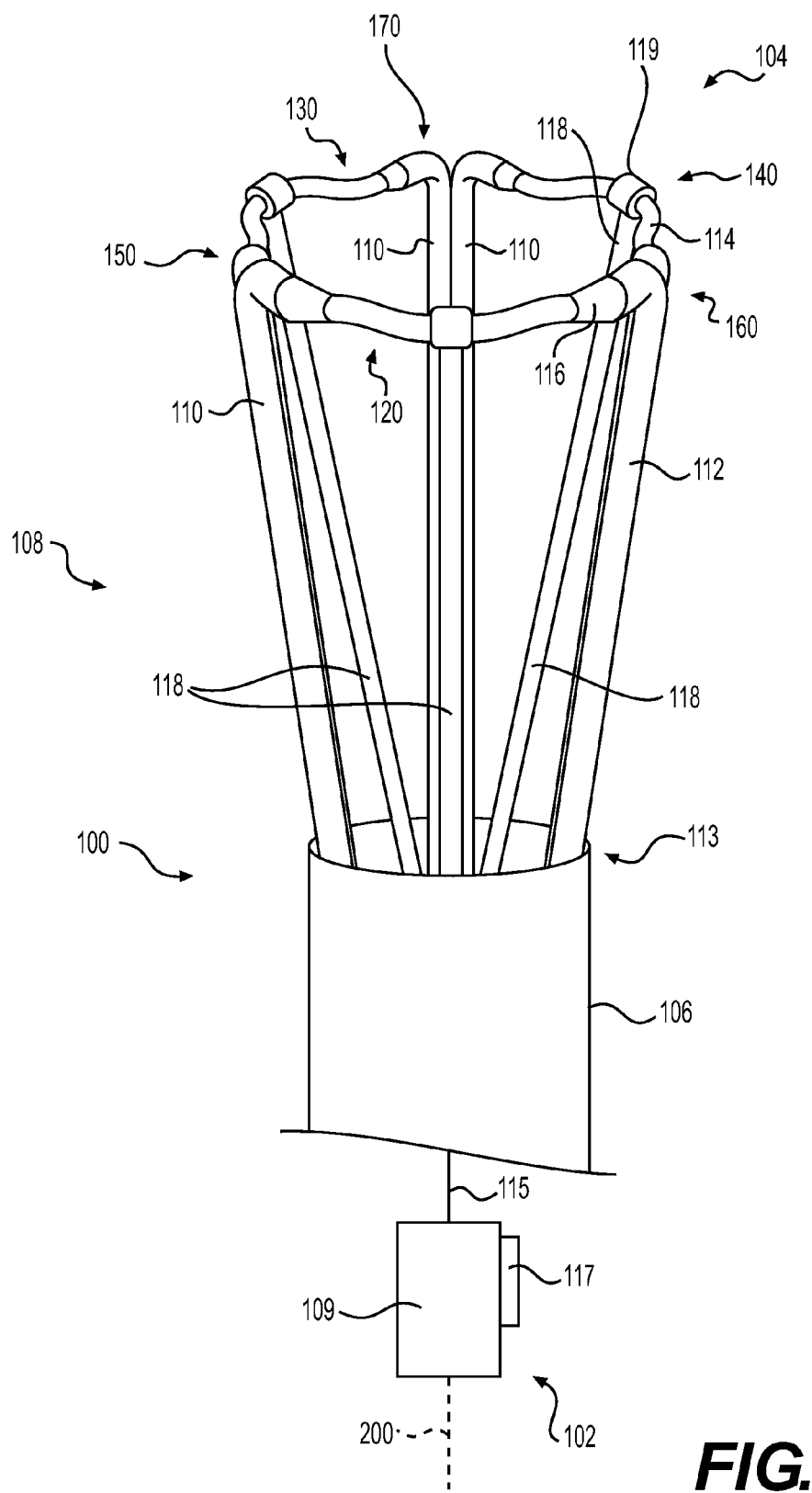
FIG. 1 is a partial side perspective view of a medical retrieval device in an expanded configuration in accordance with an embodiment of the present disclosure.
Figure 2:
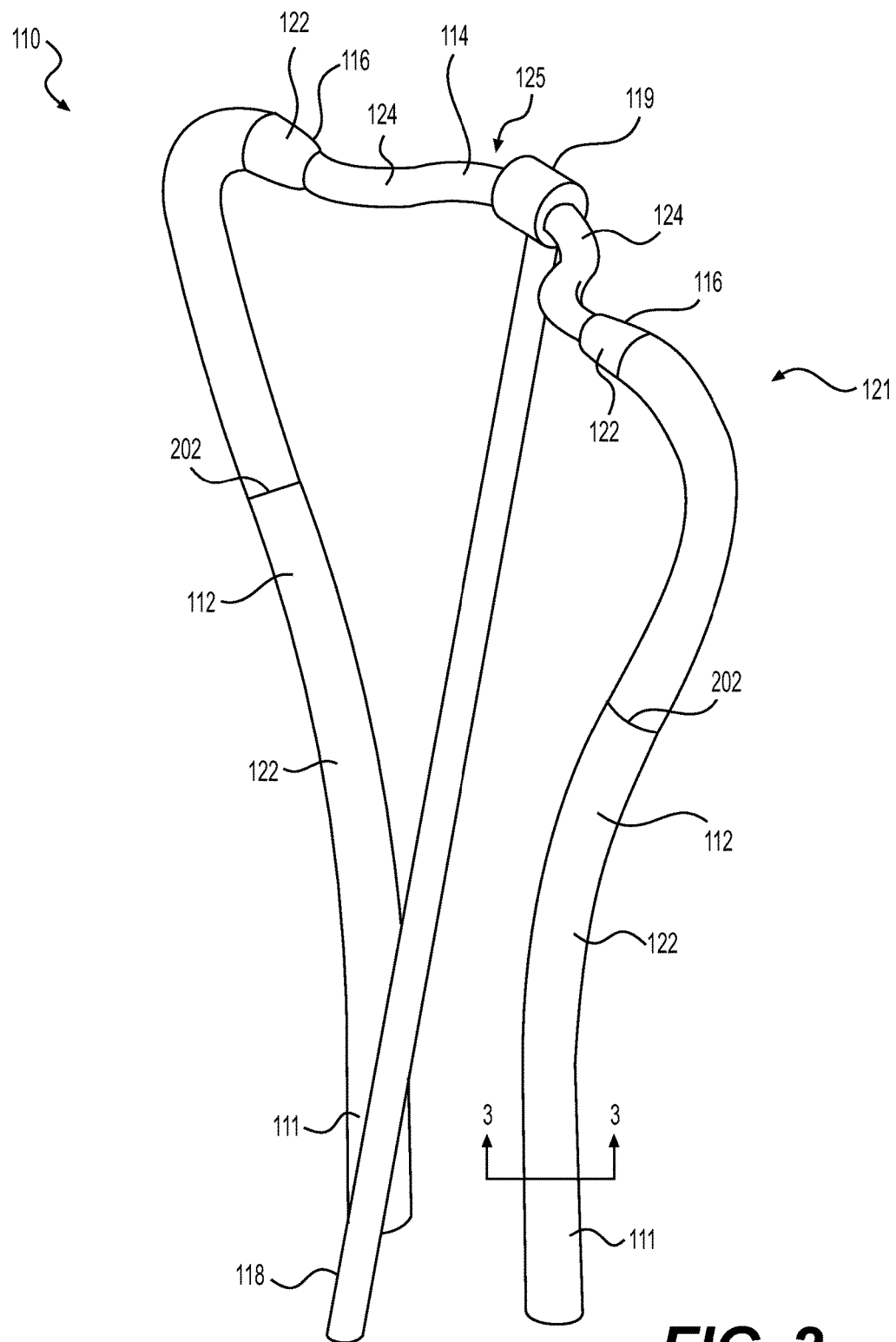
FIG. 2 is a partial side perspective view of a grasping member utilized in the medical retrieval device of FIG. 1.

As shown in FIGS. 1 and 2, a medical device 100 according to an exemplary embodiment of the present disclosure may extend from a proximal end 102, having a proximal handle assembly 109 and actuator 117, toward a distal end 104. Medical device 100 may include an elongate member 106, such as, e.g., a sheath. A grasping assembly 108 may extend distally from a distal end 113 of elongate member 106. Grasping assembly 108 may include a plurality of grasping members 110, with a proximal end of the grasping member 110 secured to elongate member 106 by any suitable mechanism such as, e.g., adhesives, welding, or the like.

As best shown in FIG. 2, each grasping member 110 may include a pair of first sections 112 that extend distally from a proximal end 111. Grasping member 110 may also include a second section 114 at a distal end 121 of the grasping member 110. As shown in FIG. 2, second section 114 may extend between a pair of first sections 112. A third section 116 of grasping member 110 may be disposed between the at least one first section 112 and the second section 114. In an alternative embodiment, one or more first sections 112 may be directly connected to second section 114 without an intervening third section 116.

As shown in FIG. 3, each first section 112 may be formed from a first, outer material 122 and a second, core material 124. In some embodiments, the first section 112 may have a different stiffness (e.g., may be stiffer) than the second section 114. Outer material 122 may be a coating or sheath formed circumferentially around the core material 124 by any appropriate manner such as, e.g., depositing, pressing, rolling, wire drawing or the like. First section 112 may also include a plurality of notches 202 (shown only in FIG. 2) that create additional surface area for gripping materials, such as, e.g., stones. The notches 202 may partially or completely extend through outer material 122, and in some embodiments, extend partially into core material 124. Further, notches 202 may reduce stiffness and facilitate localized bending of first sections 112. Additional notches 202 may also be disposed along first section 112, second section 114, and/or third section 116. Additionally or alternatively to notches 202, one or more of pitting, scraping off material layers, grooving, or the like may be utilized to increase the flexibility of one or more of first section 112, second section 114, and/or third section 116. In one embodiment, one or more of first section 112, second section 114, and/or third section 116 can be reinforced by choice of material, ribs, annealing, chemical etching or deposition, geometry, or other suitable mechanisms for reinforcing material properties.

Second section 114 may include only the core material 124. The outer material 122 and the core material 124 may both be formed of metals, though other suitable materials are also contemplated. In one embodiment, the outer material 122 may be Cobalt-Chromium, stainless steel, or the like, and the core material 124 may be a superelastic or shape memory metal such as, e.g., Nitinol, or the like. Each third section 116 may include both the outer material 122 and the core material 124. In some embodiments, the thickness of the outer material 122 in third section 116 may gradually decrease or taper toward second section 114, although other alternative thickness configurations are also contemplated. Thus, third section 116 may have a variable stiffness along its length, and may have a stiffness in between that of first section 112 and second section 114. For example, third section 116 may have a lower stiffness than first section 112, but a higher stiffness than second section 114.

As best seen in FIGS. 2 and 4, grasping member 110 of grasping assembly 108 may be formed by a continuous length of the core material 124. That is, a continuous length of core material 124 may extend through a first first section 112, a first third section 116, a second section 114, a second third section 116, and a second first section 112. Second section 114 may thus be a middle region of the continuous length of core material 124 containing at least the midpoint of the continuous length of core material 124. In an alternative embodiment, the core material 124 may be formed by a plurality of lengths of core material 124 that are joined together. In some embodiments, outer material 122 and core material 124 may be formed of the same material having different material properties resulting from, e.g., different treatments. In some embodiments, outer material 122 may have a first material property and core material 124 have a second material property.

In an unstressed state, second section 114 may have a generally bell-curve shape including a centrally located U-shaped (or bent) portion 125 extending in a radial direction. U-shaped portion 125 may be a central, preformed bend. U-shaped portion 125 may alternatively be non-curved, V-shaped, or have another suitable shape. Second section 114 may extend in a plane substantially orthogonally to a longitudinal axis of medical device 100. In some embodiments substantially orthogonally to the longitudinal axis may be approximately 90° offset from the longitudinal axis. In another embodiment, substantially orthogonally to the longitudinal axis may be approximately 89-91° offset from the longitudinal axis. In yet another embodiment, substantially orthogonally to the longitudinal axis may be approximately 80-100° offset from the longitudinal axis. In yet another embodiment, substantially orthogonally to the longitudinal axis may be approximately 45-135° offset from the longitudinal axis. In yet another embodiment, U-shaped portion 125 may be offset from the longitudinal axis. However, alternative suitable shapes and configurations of first section 112 and second section 114 are also contemplated. The first sections 112 of grasping member 110 each may include a proximal straight section 126 and a distal hook-shape section 128. The first sections 112 may also be shaped as mirror images of each other, although other suitable configurations are also contemplated. It should be noted that any portion of first sections 112, second sections 114, and/or third sections 116 may be formed of a polymer, metal, or combination of metals.

Second section 114 may be coupled to an actuation member 118 via a link 119. Link 119 may be a ring member disposed around second section 114, for example, at the peak of the U-shaped portion 125. Link 119 may be slidably, rotatably, or fixedly attached to second section 114. Actuation member 118 may be a filament, braided wire, rope, rod, or other suitable actuation member that may be coupled to actuator 117 of handle assembly 109 (referring to FIG. 1). As shown in FIG. 1, the actuation member 118 of each grasping member 110 may be coupled together at an actuation rod 115 that is proximal of the grasping members 110, and the actuator rod 115 may be coupled to the actuator 117. The activation of actuation member 118 may include any other suitable actuation assembly configured to reciprocally move actuation member 118 in a longitudinal direction including, but not limited to, sliding mechanisms, rotating mechanisms, twisting mechanisms, pushing mechanisms, pulling mechanisms, Bowden actuators, or the like.

In an alternative embodiment, medical device 100 may be activated without a separate actuation member 118. In such embodiments, medical device 100 may be moved between the retracted configuration and the expanded configuration by applying a force (e.g., pushing or pulling) to the proximal or distal ends of the grasping members 110. In one embodiment, medical device 100 may be moved between the retracted and expanded configuration by pushing or pulling sheath 106.

Referring back to FIG. 1, the plurality of grasping members 110 may include three grasping members 120, 130, and 140 that are all substantially similar to one another. Grasping members 120, 130, and 140 may each extend distally from distal end 113 of elongate member 106 and may be substantially evenly spaced about a longitudinal axis 200 of medical device 100. While three grasping members are depicted in the embodiment of FIG. 1, another suitable number of grasping members may alternatively be utilized.

All or substantially all of a given first section 112 of a grasping member 120, 130, and 140 may be coupled to all or substantially all of a first section 112 of an adjacent grasping member 120, 130, and 140 by adhesives, welding, friction, press fits, or the like. However, it is also contemplated that less than all or substantially all of adjacent first sections 112 may be coupled together. For example, a first section 112 of grasping member 120 may be coupled to a first section 112 of grasping member 130 to form a first arm 150. Another first section 112 of grasping member 120 may be coupled to a first section 112 of grasping member 140 to form a second arm 160. Another first section 112 of grasping member 130 may be coupled to another first section 112 of grasping member 140 to form a third arm 170. First arm 150, second arm 160, and third arm 170 may be disposed approximately 120° from one another, although other suitable configurations are also contemplated. Grasping members 120, 130, and 140 may thus form a basket having arms 150, 160, and 170. The basket may be movable from a refracted or collapsed configuration to an expanded configuration via movement of actuation members 118 proximally. Alternatively, medical device 100 may be configured to move from the refracted to the expanded configuration via movement of actuation members 118 distally. In an alternative embodiment, medical device 100 may be moved between the retracted and expanded configurations by the relative longitudinal movement of elongate member 106 and the proximal ends of grasping members 120, 130, and 140. Thus, in some embodiments, actuation member 118 may not be necessary.

Figure 5:
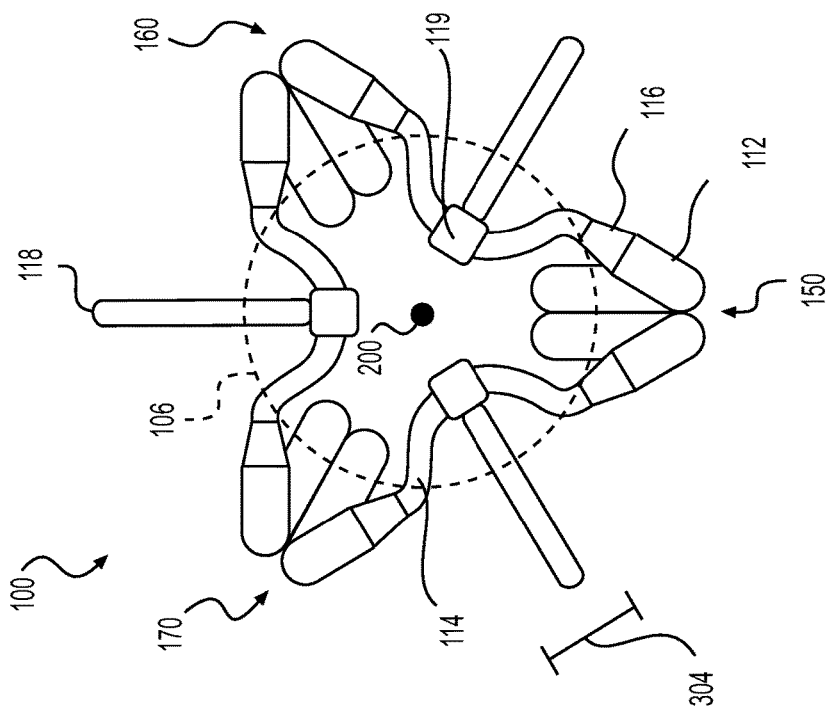
FIG. 5 is a top view of the medical retrieval device of FIG. 1 in an expanded configuration.
Figure 6:
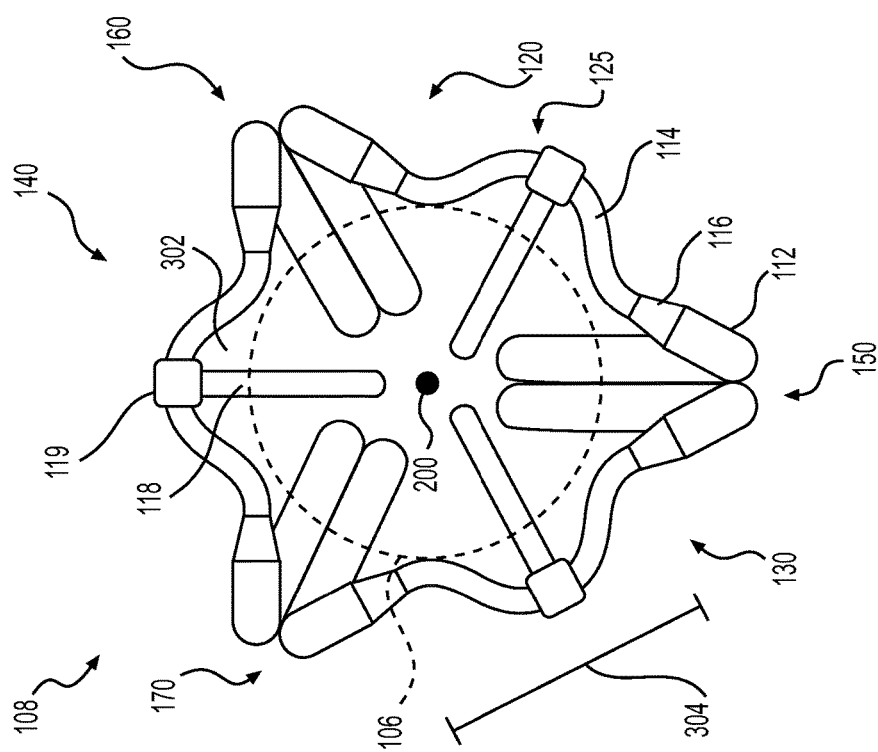
FIG. 6 is a top view of the medical retrieval device of FIG. 1 in a refracted configuration.

As seen in FIGS. 5 and 6, grasping members 120, 130, and 140 may extend both distally from elongate member 106 and radially outward from longitudinal axis 200. That is, the proximal ends 111 of grasping members 120, 130, and 140 may be disposed closer to longitudinal axis 200 than distal ends of grasping members 120, 130, and 140. In the expanded basket configuration depicted of FIG. 5, actuation members 118 may extend both distally from elongate member 106 and radially outward from longitudinal axis 200. That is, a distal end 302 of actuation member 118 may be offset from longitudinal axis 200. Further, in the expanded configuration, the U-shaped portion 125 of second sections 114 may extend outwardly from longitudinal axis 200 (e.g., the base of the U-shaped portion 125 of second sections 114 may extend outwardly from longitudinal axis 200 in a plane substantially orthogonal to longitudinal axis 200). In the expanded configuration, a gap 304 may be disposed between first sections 112 of the same grasping member 120, 130, and 140.

As noted above, a distally-directed force may be applied to actuation members 118 via actuator 117 to move medical device 100 from the expanded configuration of FIG. 5 to the retracted configuration of FIG. 6. In the retracted configuration, actuation members 118 may bow radially outward and direct second sections 114 inward toward longitudinal axis 200, thus also directing grasping members 120, 130, and 140 inward toward longitudinal axis 200. The curvature of second sections 114 may extend inwardly toward longitudinal axis 200 (e.g., the base of the U-shaped portion 125 of second sections 114 may extend inwardly toward longitudinal axis 200 and in a plane substantially orthogonal to longitudinal axis 200). U-shaped portion 125 may move from the expanded to the retracted configuration by rotating toward longitudinal axis 200. In some embodiments, U-shaped portion 125 may rotate approximately 180° toward longitudinal axis 200, although other suitable rotations are also contemplated. U-shaped portion 125 may follow an arc-like trajectory, a linear trajectory, or another suitable trajectory while moving between the expanded and retracted configurations. In the retracted configuration, gap 304 between first sections 112 of the same grasping member 120, 130, and 140 may be smaller than when medical device 100 is in the expanded configuration. In one embodiment, the distally-directed force may be released from (and/or a proximally-directed force applied to) actuation member 118 to move medical device 100 from the retracted configuration of FIG. 6 to the expanded configuration of FIG. 5.

The disclosed medical devices may be utilized in any suitable application requiring the capture and removal of materials from the body. The disclosed medical devices may be simple and inexpensive to manufacture, and have improved durability. In particular, the disclosed medical devices may help eliminate the wear and fatigue associated with medical devices utilizing a more complex system of tubes and wires. The disclosed medical devices may also reduce the empty space between components to achieve a reduced profile. The disclosed medical devices may also provide an advantageous increased area for load bearing members.

Any aspect set forth in any embodiment may be used with any other embodiment set forth herein. The devices and apparatus set forth herein may be used in any suitable medical procedure, may be advanced through any suitable body lumen and body cavity, and may be used to remove material from any suitable body portion. For example, the apparatuses and methods described herein may be used through any natural body lumen or tract, including those accessed orally, vaginally, rectally, nasally, urethrally, or through incisions in any suitable tissue.

The disclosed medical devices may be configured to capture fragments having dimensions of about 3 french or smaller. In some embodiments, the disclosed medical devices may be able to capture and release smaller stones having diameters from 1 mm to 12 mm. In some embodiments, a user may want to reposition larger stones from the lower calyx to the upper calyx of the kidney to be broken with a laser before removing them through a small diameter of the ureter. The stones may be removed in front of a scope, as opposed to through scope channel to prevent damage to a scope channel. When stones are removed, both an endoscope and a medical device may be removed from the human body. In some embodiments, a guide sheath for a ureteroscope may be used to guide the ureteroscope and medical device back to a previous position or to a new position to capture additional stones, and protect a ureter wall during stone removal. While moving from the expanded configuration to the unexpanded configuration, medical devices of the present disclosure may ligate larger stones and capture smaller stones within a basket.

It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only. The following disclosure identifies some other exemplary embodiments.

We claim:

1. A medical device, comprising:
   a member;
   at least one actuation member;
   a plurality of grasping members extending from the member, each of the grasping members including:
   a proximal end;
   a distal end;
   at least one first section being formed of a first material and a second material; and
   a second section located at the distal end of the grasping member, the second section being formed without the first material and having a different stiffness than the at least one first section,
   wherein, in an expanded configuration, the second section further includes a bent portion that extends radially outward from a longitudinal axis of the medical device, and
   wherein the at least one actuation member is coupled to the second section of at least one grasping member and at least partially surrounds at least a portion of the bent portion.

2. The medical device of claim 1, further including at least one notch disposed along the at least one first section.

3. The medical device of claim 1, wherein the first material is disposed around the second material in the first section.

4. The medical device of claim 1, further including at least one third section disposed between the at least one first section and the second section, the at least one third section being formed of the first material and the second material, the thickness of the first material in the at least one third section being less than a thickness of the first material in the at least one first section.

5. The medical device of claim 4, wherein the thickness of the first material in the at least one third section surrounds the second material in the at least one third section and tapers toward the second section.

6. The medical device of claim 1, wherein the plurality of grasping members are reciprocally movable between a retracted configuration and the expanded configuration.

7. The medical device of claim 6, wherein the second section lies in a plane that extends substantially orthogonal to the longitudinal axis of the medical device.

8. The medical device of claim 6, wherein the movement of the at least one actuation member moves the at least one grasping member from the retracted configuration to the expanded configuration.

9. The medical device of claim 6, wherein the plurality of grasping members extend distally from the member and extend radially outward from the longitudinal axis of the medical device such that the proximal ends of the grasping members are closer to the longitudinal axis than the distal ends of the grasping members.

10. The medical device of claim 1, wherein the at least one actuation member includes a link disposed around at least a portion of the bent portion.

11. The medical device of claim 10, wherein, in the retracted configuration, the bent portion extends radially inward toward the longitudinal axis of the medical device.

12. The medical device of claim 1, wherein each grasping member is formed from a continuous length of second material.

13. The medical device of claim 12, wherein a middle region of the continuous length of second material corresponds to the second section of each grasping member.

14. The medical device of claim 1, wherein the plurality of grasping members includes three grasping members coupled to one another to form a basket or a grasper.

15. A medical device, comprising:
   a member;
   a plurality of grasping members extending from the member, each of the grasping members including:
   a proximal end;
   a distal end disposed further away from a longitudinal axis of the medical device than the proximal end;
   at least one first section being formed of a first material having a first material property and a second material having a second material property; and
   a second section located at the distal end of the grasping member, the second section being formed without the first material and having a different stiffness than the at least one first section, wherein, in an expanded configuration, the second section further includes a bent portion that extends radially outward from a longitudinal axis of the medical device; and
   a plurality of actuation members directly coupled to the second section and at least partially surrounding at least a portion of the bent portion, wherein the plurality of actuation members are configured to expand and/or contract the grasping members.

16. A medical device, comprising:
   a basket or grasper having a plurality of arms movable between a retracted configuration and an expanded configuration, the basket or grasper being formed by a plurality of grasping members, each grasping member having:

a proximal end;

a distal end;

a plurality of first sections being formed of an outer material and a core material; and a second section located at the distal end of the grasping member, the second section being formed with only the core material, and having a different stiffness than each of the plurality of first sections, wherein each of the plurality of arms are formed by joined first sections of adjacent grasping members, and wherein in the expanded configuration, the second section includes a bent portion that extends radially outward from a longitudinal axis of the medical device; and an actuation member coupled to the second section and at least partially surrounding at least a portion of the bent portion.

17. The medical device of claim 16, wherein:

a first of the plurality of arms is formed by joined first sections of a first and a second of the plurality of grasping members;

a second of the plurality of arms is formed by joined first sections of the second and a third of the plurality of grasping members; and a third of the plurality of arms is formed by joined first sections of the third and the first of the plurality of grasping members.

18. The medical device of claim 16, wherein each of the plurality of arms extends radially outward about a longitudinal axis of the medical device when the basket or grasper is in the expanded configuration.

* * * * *